United States Patent
Guracar

(10) Patent No.: US 7,713,209 B2
(45) Date of Patent: May 11, 2010

(54) TARGETED CONTRAST AGENT IMAGING WITH MEDICAL DIAGNOSTIC ULTRASOUND

(75) Inventor: Ismayil Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 406 days.

(21) Appl. No.: 11/805,151

(22) Filed: May 21, 2007

(65) Prior Publication Data
US 2008/0294049 A1 Nov. 27, 2008

(51) Int. Cl.
*A61B 8/14* (2006.01)
*A61B 8/00* (2006.01)

(52) U.S. Cl. .................... 600/458; 600/443
(58) Field of Classification Search .......... 600/437, 600/443, 454–458; 382/128
See application file for complete search history.

(56) References Cited

U.S. PATENT DOCUMENTS

| | | | |
|---|---|---|---|
| 6,436,041 B1 * | 8/2002 | Phillips et al. | 600/437 |
| 6,602,195 B1 | 8/2003 | Krishnan et al. | |
| 6,632,177 B1 | 10/2003 | Phillips et al. | |
| 6,638,228 B1 | 10/2003 | Brock-Fisher et al. | |
| 6,682,482 B1 | 1/2004 | Krishnan | |
| 6,814,703 B2 * | 11/2004 | Sato | 600/458 |
| 7,004,906 B1 | 2/2006 | Guracar | |
| 2003/0229285 A1 | 12/2003 | Simpson et al. | |
| 2007/0014445 A1 | 1/2007 | Lin | |
| 2007/0073144 A1 | 3/2007 | Simpkin | |
| 2007/0073146 A1 * | 3/2007 | Phillips et al. | 600/437 |

FOREIGN PATENT DOCUMENTS

| | | |
|---|---|---|
| EP | 1767961 A1 | 3/2007 |
| WO | WO 2006/015971 A1 | 2/2006 |
| WO | WO 2007/054544 A1 | 5/2007 |

OTHER PUBLICATIONS

U.S. Appl. No. 11/713,209, filed on Mar. 2, 2007.
PCT International Search Report for PCT/US2008/004358, dated Jul. 25, 2008, 6 pgs.

* cited by examiner

*Primary Examiner*—Eric F Winakur
*Assistant Examiner*—Michael T Rozanski

(57) ABSTRACT

Contrast agent enhanced medical diagnostic imaging is provided. Substantially stationary or bound contrast agents are detected. By tracking relative motion between frames of data, spatial locations associated with consistent detection of contrast agents are identified. The contrast agent detected at the identified spatial locations are substantially stationary contrast agents.

19 Claims, 1 Drawing Sheet

TARGETED CONTRAST AGENT IMAGING WITH MEDICAL DIAGNOSTIC ULTRASOUND

BACKGROUND

The present embodiments relate to contrast agent enhanced medical diagnostic ultrasound imaging. In particular, imaging of particular contrast agents is performed.

Typically, contrast agents injected into a patient flow through the circulatory system. However, researchers are currently designing ultrasound contrast agents targeted to specific tissues. For example, agents can be designed to attach to areas of inflammation or other molecular receptors using ligands or other surface treatment on the contrast agents. Targeted contrast agents may bind to corresponding proteins on the endothelium or plaque. As one of many examples where contrast agents can be indicative of more than just where blood is flowing, contrast agents can attach to damaged endothelial cells within a vessel. Increased enhancement in contrast agent ultrasound detection is observed on the wall of the vessel.

Stationary contrast agents may be imaged, such as disclosed in U.S. Published Application No. 20070073146. A processor distinguishes different types of contrast agents or contrast agents in different binding states with relative signal strength or velocity. Monitoring absolute signal strength as a function of time may indicate binding. U.S. Pat. No. 7,004,906 discloses using a coherent technique (i.e. color Doppler) for detecting and color-coding stationary agent.

BRIEF SUMMARY

By way of introduction, the preferred embodiments described below include methods, systems, computer readable media, and instructions for contrast agent enhanced medical diagnostic imaging. Substantially stationary or bound contrast agents are detected. By tracking relative motion between frames of data, spatial locations associated with consistent detection of contrast agents are identified. The contrast agents detected at those locations are substantially stationary contrast agents.

In a first aspect, a method is provided for contrast agent enhanced medical diagnostic ultrasound imaging. A sequence of ultrasound frames of data representing, at least in part, information from contrast agents is generated. The relative position between at least first and second ultrasound frames of data of the sequence is tracked. Substantially stationary contrast agents are identified from the sequence as a function of the tracking and a consistency of response.

In a second aspect, a computer readable storage medium has stored therein data representing instructions executable by a programmed processor for contrast agent enhanced medical diagnostic ultrasound imaging. The storage medium includes instructions for detecting contrast agents, correcting for motion between frames of ultrasound data corresponding to the detected contrast agents, and identifying contrast agents that are substantially stationary from the motion corrected frames of ultrasound data by consistency of return from one or more spatial locations.

In a third aspect, a system is provided for contrast agent enhanced medical diagnostic ultrasound imaging. An image processor is operable to detect contrast agents from information output from a receive beamformer. A motion processor is operable to stabilize for motion between frames of ultrasound data and operable to determine contrasts agents with substantially no movement between the stabilized frames of ultrasound data. The determining is a function of consistent response at one or more locations. A display is operable to display an image of the contrast agents with substantially no movement uniquely colored.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Targeted contrast agents attach to an area of interest in the body. The contrast agents and body are imaged, producing contrast agent and tissue information over a period, such as several seconds to minutes. The tissue information is used for tracking. The contrast agent information is stabilized, such as by aligning data to counter any motion. After alignment, consistency of contrast agent response at one or more spatial locations indicates stationary contrast agent. For display, contrast agents, which are stationary, may be specially color-coded. Therapeutic levels of ultrasound or other treatment can be directed to areas where agent has attached.

In one example embodiment, the contrast agent information of the sequence is integrated using maximum intensity projection (MIP). If the field of view changes (i.e. elevation plane or large position changes) MIP can be suspended. In other example embodiments, the contrast agent imaging is combined with contrast agent destruction for wash-in time, parametric imaging, or saturation detection. The destruction occurs before or after detection of stationary contrast agents.

Figure 1:
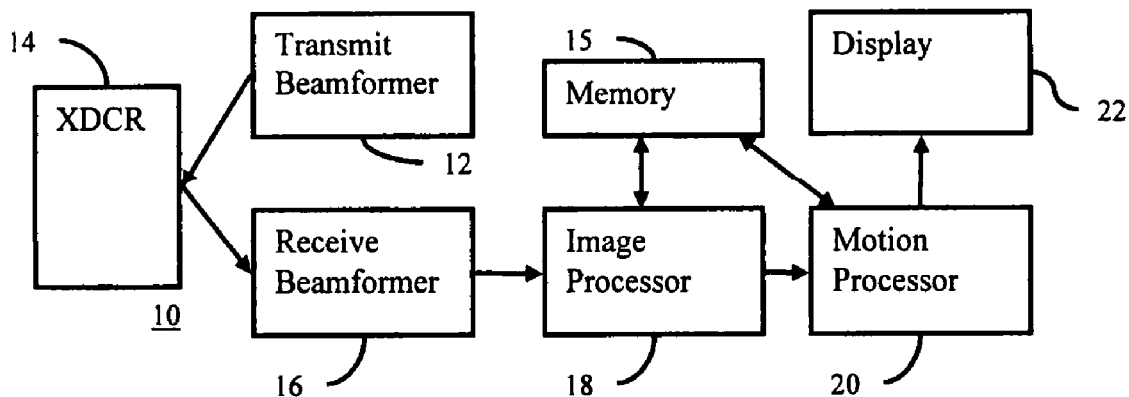
FIG. 1 is a block diagram of one embodiment of an ultrasound imaging system for contrast agent enhanced imaging.

FIG. 1 shows a system 10 for enhanced contrast agent medical diagnostic ultrasound imaging. The system 10 includes a transmit beamformer 12, a transducer 14, a memory 15, a receive beamformer 16, an image processor 18, a motion processor 20, and a display 22. Additional, different, or fewer components may be provided. For example, the motion processor 20 is combined with or part of the image processor 18.

The system 10 is a medical diagnostic ultrasound imaging system in one embodiment, but other imaging systems of the same (ultrasound) or different modality may be used. In other embodiments, part or all of the system 10 is implemented in a computer or workstation. For example, previously acquired frames of data are processed without the beamformers 12, 16 or transducer 14.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. The transmit beamformer 12 may cause the beam to have a particular phase and/or amplitude. For example, the transmit beamformer 12 transmits a sequence of pulses associated with a given scan line or to adjacent scan lines. The pulses correspond to beams with different amplitudes and/or relative phases. In alternative embodiments, a single beam is used for any given scan line and/or beams with a same amplitude and/or relative phases are used.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. The elements are piezoelectric or capacitive membrane based structures. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. The focused information from the channels are summed dynamically. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band.

Any desired sequence of transmit and receive operation may be used to obtain ultrasound information. For example, B-mode data may be obtained by scanning a region once. The B-mode may be used for tissue imaging. Correlation or motion tracking may be used to derive fluid information from B-mode data. B-mode operation may provide contrast agent information, such as by filtering to isolate information at a second harmonic. Doppler information may be obtained by transmitting sequences of beams along each scan line. A corner turning memory may be used to isolate tissue, contrast agents, and/or flow information from Doppler signals. Other now known or later developed modes may be used.

In one embodiment, the mode is a contrast agent imaging mode. Contrast agents may be imaged with typical B-mode or Doppler techniques. Contrast agent information is information primarily responsive to contrast agents, and tissue information is information primarily responsive to tissue. Isolating information at the second, even, odd, sub, or other harmonics may more likely identify information from contrast agents. For example, a two-pulse technique is used. The pulses have a same amplitude, but different phase. By summing the response, information associated with even harmonics is identified. Filtering may alternatively be used. Alternatively or additionally, relative phasing is provided in the receive processing.

In one embodiment, the transmit sequence is controlled to generate echo signals responsive to the cubic fundamental. The beamformer 12 is operable to transmit a plurality of pulses having at least two different amplitude levels and at least two of the plurality of pulses having opposite or different phases. Transmitter power can be varied in any suitable manner, as for example by adjusting the voltage applied to individual transducer elements, or by adjusting the number of transducer elements (or transmit aperture) used to form a particular pulse.

For obtaining ultrasound data at the cubic fundamental, the receive beamformer 16 includes line memories and a summer or a filter to combine signals responsive to the transmissions. The line memories or buffers can be formed as physically separate memories or can be formed as selected locations in a common physical device. The beamformed signals are stored in the line memories or buffers and then weighted and summed in a weighted summer. Weighting values for both amplitude and phase are used in the weighted summer. The memories and the summer can be implemented using analog or digital techniques. The weighted summer forms a composite output signal by weighting the separate beamformed receive signals. The composite output signal for a given spatial location is a sample associated with the cubic fundamental response.

Obtaining cubic fundamental information is disclosed in U.S. Pat. No. 6,494,841, the disclosure of which is incorporated herein by reference. Any of the transmit sequences and receive combinations disclosed therein may be used for obtaining cubic fundamental information. Other transmit sequences and receive combinations for obtaining cubic fundamental information may be used, such as disclosed in U.S. Pat. Nos. 6,602,195, 6,632,177, 6,638,228 and 6,682,482, the disclosures of which are incorporated herein by reference. In general, a sequence of pulses with different amplitudes and phases are transmitted. Using amplitude change or different amplitudes without different phases may also be used to obtain cubic fundamental information. By combining received signals responsive to the sequence, a sample including cubic fundamental information is obtained. The cubic fundamental information is highly specific to ultrasound contrast agents since contrast agents produce cubic response and the transducer and tissue produce very little cubic response. The information provides tissue clutter rejection, allowing for imaging more specific to contrast agents. For example, small vessels within tissue may be more easily imaged or identified using cubic fundamental information.

The image processor 18 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof or other now known or later developed device for detecting information for display from beamformed ultrasound samples.

In one embodiment, the image processor 18 implements a fast Fourier transform from a plurality of samples representing a same region or gate location. Each of the samples is responsive to cubic fundamental so that a pulsed wave Doppler display may be generated from cubic fundamental information. The image processor 18 also includes a B-mode detector in a parallel track. The B-mode detector operates on the same or different beamformed samples to detect tissue, contrast agent, or tissue and contrast agent response. For example, one receive beam for each spatial location from the sequence of receive beams used for cubic fundamental isolation is applied to the B-mode detector for imaging primarily tissue information.

The image processor 18 outputs frames of ultrasound data. The frames of data are formatted in an acquisition format (e.g., polar coordinate), a display format (e.g., scan converted into a Cartesian coordinate format or an image), or other format. Each frame of data represents a one, two, or three-dimensional scanned region. The frames of data include a single or multiple types of data. For example, one frame of data includes just contrast agent information. As another example, one frame of data includes contrast agent information for some spatial locations and another type of information (e.g., B-mode or Doppler) for other spatial locations. Different types of data may be provided in the same frame for a same spatial location. In another example, the different types of data are provided in different frames of data.

In an alternative embodiment, the image processor 18 loads data from a network or memory 15. For example, DICOM or other images are loaded. Each image is a frame of data. One frame may include different types of data, one overlaid on another. Alternatively, each frame includes only one type of data with different frames for different data types. In another embodiment, each frame is subdivided so that one portion includes one type of data and another portion includes another type of data with or without overlap of the represented spatial locations.

The motion processor 20 is an application specific integrated circuit, correlation processor, Fourier transform processor, general processor, control processor, field programmable gate array, digital signal processor, analog circuit, digital circuit, buffer, memory, combinations thereof, or other now known or later developed device for determining relative motion between frames of data and of detected contrast agent. The motion processor 20 receives the frames of data to stabilize for motion between frames of ultrasound data. For example, B-mode or tissue information is used to track motion between frames, and the same information and contrast agent information are aligned from frame-to-frame based on the tracked motion.

The motion processor 20 may determine contrasts agents with substantially no movement between the stabilized frames of ultrasound data. After alignment or based on the tracked motion, substantially stationary contrast agents may be identified. Substantially is used to account for errors in tracking, motion of the tissue to which the contrast agents may be bound, or other apparent motion in bound contrast agents. By identifying spatial locations with consistent response from contrast agents, stationary contrast agents may be identified. Region identification may be used, such as identifying small regions (e.g., 2×2 region) with contrast agent response. When a threshold number of frames, such as a majority of the frames of contrast agent information, indicate contrast agent response at a region, stationary contrast agents are identified.

In another embodiment, the frames of ultrasound data are combined. By integrating from a plurality of frames of detected contrast agents, a threshold may be applied to identify locations with stationary contrast agents.

The motion processor 20 generates an image for the display 22. The image is generated from one or more frames of ultrasound data. For example, contrast agent information for a single frame or sequence of frames is color coded as a function of the stationary determination. Where a spatial location for a given frame indicates contrast agent and is associated with stationary contrast agent, the detected contrast agents are colored or otherwise highlighted differently than other contrast agents. In other embodiments, spatial locations associated with stationary contrast agents are displayed to show stationary contrast agent regardless of whether contrast agents were detected at the location in a particular frame of data.

Another example display is a combination of data from a plurality of frames of data. The motion processor 20 may include a persistence filter, other filter, summer, alpha blending buffer, other buffer, memory, processor, adder, or other device for generating an image from information of different frames of data. For example, the motion processor 20 compares data for a particular spatial location from one frame to another frame or an ongoing combination frame. Based on the comparison (e.g., highest value, contribution to mean value, or lowest value), one of the values is selected or the ongoing combination frame is updated to include the desired value. As another example, the motion processor 20 determines an average, total, or other value representing a location or region as a function of time.

The display 20 is a CRT, monitor, LCD, flat panel, projector or other display device. The display 20 receives display values for displaying an image. The display values are formatted as a one-dimensional image, two-dimensional image, or three-dimensional representation. In one embodiment, the display values are for an image generated as a function of frames of data acquired at different times, such as a time intensity curve (TIC) or maximum intensity projection (MIP) image. As additional frames of data are acquired and selected, the image may be updated. Other images, such as images from single or component frames of data, may also be displayed.

In the image, one or more spatial locations (e.g., pixels) are modulated as a function of the determination of contrast agents with substantially no movement. For example, such pixels are uniquely colored. Any other display of stationary contrast agents may be used, such as disclosed in U.S. Published Application No. 20070073146 or U.S. Pat. No. 7,004,906, the disclosures of which are incorporated herein by reference.

The memory 15 is a buffer, random access memory, read only memory, cache, hard drive, removable, optical, flash, system memory, combinations thereof, or other now known or later developed device for images and/or instructions. The memory 15 may be a combination of different memory devices or separately addressed regions. In one embodiment, the memory 15 stores data to be used, during use, or after processing for the processors 18 and/or 20.

The image processor 18 and/or motion processor 20 operate pursuant to instructions. A computer readable storage medium stores data representing instructions executable by one or both of these programmed processors for contrast agent enhanced medical diagnostic ultrasound imaging. The instructions for implementing the processes, methods and/or techniques discussed herein are provided on computer-readable storage media or memories 15, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 2:
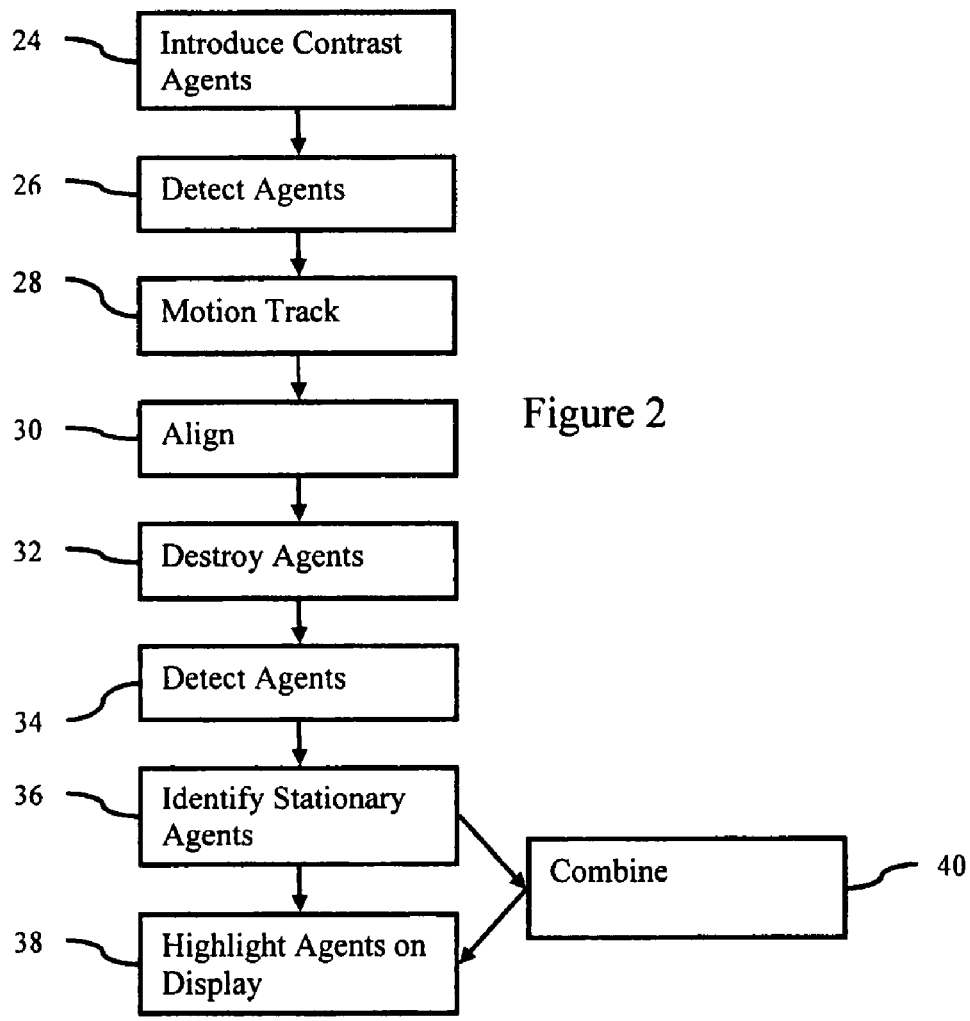
FIG. 2 is a flow chart diagram of a method for contrast agent enhanced diagnostic medical ultrasound imaging according to one embodiment.

FIG. 2 shows a method for contrast agent enhanced medical diagnostic ultrasound imaging. The method is implemented by the system 10 of FIG. 1 or a different system. The method is performed in the order shown or a different order. Additional, different, or fewer acts may be provided. For example, acts 28 and 36 are provided with none or only some of the other acts. As another example, acts 26, 32, 38, and/or 40 are optional.

In act 24, contrast agents are introduced into a patient. The contrast agents are injected as a bolus manually or with a pump through a catheter or syringe. The contrast agents are injected into the bloodstream or other conduction path. The contrast agents may be of any number. In one embodiment, a limited number of contrast agents are injected to reduce the number of free flowing contrast agents. In another embodiment, a large number of contrast agents are injected where stationary contrast agents are to be detected in areas of relatively lower perfusion.

The contrast agents are microbubbles with or without a shell. The contrast agents may include or be formed from therapeutic material, such as drugs for the treatment of a patient. The surface of the contrast agents may bind to or stick to tissue. In one embodiment, the contrast agents include ligands or other material or structure to more likely bind or stick to tissue. The material or structure may be targeted to bind or stick to specific tissues, such as deceased or inflamed tissue.

In act 26, a sequence of ultrasound frames of data is generated. The sequence is generated by acquiring frames of data with ultrasound, or by acquiring previously generated ultrasound frames of data (e.g., DICOM images). The frames of data are acquired in real time with live scanning or are from stored clips. The sequence may be substantially continuous or periodic (e.g., acquired once or more every heart cycle).

The sequence includes frames of data representing a scanned region at different times. Each frame of data represents a same or overlapping region. Some frames may represent different regions, such as due to out-of-plane motion of the transducer relative to the patient.

Contrast agents are detected. The region includes contrast agents or an area likely to include contrast agents after insertion of the agents. The contrast agents respond to ultrasound energies. Some or all of the frames of data include information from contrast agents. The information may also include response from tissue or fluids. In one embodiment, the information is obtained at a cubic fundamental of ultrasound signals. For example, ultrasound signals are transmitted in a plurality of pulses having at least two different amplitude levels and phases. To avoid or minimize destruction of the contrast agents, low amplitude transmissions (e.g., MI less than 0.7) are used. Signals responsive to the transmissions are combined. Data is acquired at each spatial location of a region of interest in each frame of data.

The intensity, variation, velocity, power, or other characteristic of the response of the contrast agents is determined. In one embodiment, a B-mode detector is used for both contrast agent and tissue information detection. Alternatively, a separate detector, such as Doppler or other detector, is used to detect contrast agent information. The contrast agent information is detected using any technique with specificity to contrast agents. The same receive beamformed information or separate information is also used for determining the spatially registered B-mode or tissue information.

Only one type of data is represented in the frames of data, such as data representing just contrast agents or responses from contrast agent and tissue. Alternatively, the frames of data represent different types of data, such as in a same frame or in different sets of frames.

In acts 28 and 30, the processor corrects for motion between frames of ultrasound data. Due to patient or transducer movement between acquisitions of frames of data, the scanned regions likely overlap, but may be shifted relative to each other. The spatial relationship between a reference frame and other frames or between sequentially adjacent frames is stabilized. For each new frame of data, the previous or temporally adjacent selected frame of data is used as the reference frame. Alternatively, the same reference frame is used for comparison to each temporally spaced frame of data.

The spatial relationship of the contrast agent information is corrected. The motion may be determined using the contrast agent information. In other embodiments, the B-mode or tissue information is used for correcting motion for both the tissue and the contrast agent information. Stabilization is performed in the acoustic domain, the Cartesian domain or any other coordinate space.

In act 28, the motion is tracked. Data from one frame of data is correlated with different regions in the other frame of data to identify a best or sufficient match. A correlation, cross-correlation, minimum sum of absolute differences, or other function indicates a level of similarity between two frames of data. By repositioning one frame of data relative to another frame of data in a search pattern, the level of match or similarity is determined for various relative positions. Any search pattern may be used, such as searching based on previous motion, course and fine search sequences, or searching based on typical motion. The position associated with the greatest similarity indicates the motion between the frames of data.

Global or local motion may be corrected. For global motion, the entire frames of data are used. Alternatively, regions of interest, such as a region about ⅓ of the total area or volume is used for comparison. The region searched may be limited, such as only searching within a particular range. For local motion, a plurality of regions may be separately tracked. A final motion is determined as a function of the motion for each sub-region, such as by averaging.

Motion is corrected by determining a relative translation and/or rotation along one or more dimensions. The motion is determined in one or more dimensions. The motion may be lateral only, in-plane for two-dimensional imaging, or along three axes for three-dimensional scanning. Optionally, an amount of rotation around or more axes may be determined.

The optional act 30 of alignment reassigns spatial locations. The spatial locations of each frame of data are reassigned based on the motion relative to the reference. The reassignment spatially aligns the ultrasound frames of data as a function of the tracking. Rigid or non-rigid correction may be used. The motion correction may remove or lessen motion associated with transducer movement, patient movement, or organ movement. As an alternative, alignment is not performed. Any spatial offset due to the motion is calculated as needed from the motion.

In act 32, contrast agents are destroyed. The user views contrast agents detected in act 26 with or without any correction of acts 28 and 30. Once the presence of contrast agents is confirmed, the contrast agents may be destroyed to calibrate or establish a desired initial condition (e.g., baseline). After destruction, the contrast agents re-perfuse the region of interest. In alternative embodiments, substantial numbers of contrast agents are not destroyed.

For destruction, acoustic energy sufficient to destroy some or all of the contrast agents is transmitted. For example, acoustic energy with a mechanical index 0.7 or higher at one or more locations is transmitted. Multiple transmit beams may be used to substantially destroy contrast agents in a given region. The region may be a region of interest or an entire field of view.

In act 34, contrast agents are detected again. The contrast agents are carried into or re-perfuse the region of interest. During and after reperfusion, the detection is the same or different than the detection of act 26. For example, a cubic fundamental response from ultrasound signals is detected.

To further isolate response from contrast agents, especially in low density circumstances, individual contrast agents may be detected. A spatial, such as two-dimensional, high pass filter is applied. Sufficiently strong response after high pass filtering indicates a single contrast agent. The response is compared with a threshold. Erosion may be used in other embodiments. In another alternative, gradient based filtering enhances single contrast agent response.

In some contrast agent detection techniques, tissue may cause undesired contrast agent detection. The tissue response to ultrasound may have a sufficiently similar response as contrast agents. Regions where contrast agent is detected immediately after destruction are identified. These regions are tissue leakage regions. These leakage signals may be detected as stationary contrast agents unless suppressed. This tissue leakage may be removed, reduced or prevented. The baseline brightness or value at the leakage regions may be subtracted for subsequent processing in act 36. The response may be colored differently than used for stationary contrast agents.

In act 36, substantially stationary contrast agents are detected. Substantially accounts for contrast agents bound to moving tissue, transducer-patient motion not fully or correctly compensated, and/or contrast agents loosely bound such that some motion results. The contrast agent information detected in act 34 is used to identify stationary contrast agents.

The motion tracking and/or alignment of acts 28 and 30 are performed with the data detected after destruction. The stationary contrast agents are identified from the sequence as a function of the tracking of act 28. The motion correction spatially aligns the frames within the sequence in acts 28 and 30, allowing identification of detected contrast agents that are substantially stationary from the frames of ultrasound data.

The contrast agent data of the detected contrast agents is examined. Contrast agents in a substantially same location in spatially aligned ultrasound frames of data are identified as stationary. Spatial locations with consistent contrast agent response adjusted by the tracking reflect stationary contrast agents.

In one embodiment, spatial locations with contrast agent response in less than all the frames are identified as stationary contrast agents. A threshold number of instances within a sequence of frames of ultrasound data is used. Once a contrast agent is detected, the number of frames that the agent is found in a particular location is counted. If the ratio of frames with contrast agent to frame without in the particular location is above a certain threshold, then the contrast agent is determined to be stationary. The threshold may be an absolute number, ratio, or other function. For example, a ⅔ or ¾ ratio is used.

To account of uncorrected motion, regions rather than points may be used. For example, 2×2, 3×3, 2×3 or 2×2×2 regions are searched. If the region includes detected contrast agents a sufficient number of times, even if not in the exact same location, substantially stationary contrast agent is identified.

In act 38, the detected stationary contrast agents are highlighted in a displayed image. Display values for corresponding spatial locations are modulated or weighted by the binary determination of stationary contrast agent. Alternatively, a color or other map is selected based on the determination. For spatial locations with stationary contrast agent, a different color or map is used than for other locations. For example, stationary contrast agents are assigned different colors than moving contrast agents. The contrast agent responses are colorized.

The contrast agent information may be overlaid with tissue information. For example, pixels corresponding to detected contrast agents are colored, and other regions are displayed as luminance or gray scale values. In other embodiments, the tissue information and the contrast agent information for a given spatial location are combined for display. For substantially stationary contrast agents, the highlighting is incorporated into the combination function.

In act 40, the substantially stationary contrast agents are displayed or highlighted in an alternative or additional embodiment. The frames of data from the sequence are combined into a maximum intensity or integration image. The data combined is for a specific type of information, such as combining the contrast agent or stationary contrast agent information. The tissue information is also combined or a single frame of tissue information is used for the underlying image.

The highlighting of act 28 may be performed prior to or after the combination. For example, the maximum intensity projection (MIP) for contrast agent responses is determined for each spatial location. Moving contrast agents are coded with darker colors. Stationary contrast agents are coded with bright colors. The coded information is combined. As another example, the contrast agent information is combined. The results are then coded.

For maximum intensity projection, the maximum value throughout the sequence is selected. For each spatial location in a region of interest, the maximum value from the spatially aligned ultrasound frames of data is determined and used for the image. For integration, a weighted combination is used. For each spatial location in a region of interest, the average or other function outputs a value used for the image.

In one embodiment, only a subset of the ultrasound frames of data from the sequence are used in the combination. For example, the frames of data are selected as a function of motion. Frames associated with a threshold amount of relative motion are not used in the combination. Frames of data when the transducer is in the proper field of view during the integration period (i.e. 20 seconds) are selected and used.

Motion correction between each frame may reduce blurring. However, certain forms of motion, such as out-of-plane motion, may not be corrected. Some blurring may still exist. To further reduce blurring or image artifacts in the combination over time, frame selection is performed based on the data acquired. Frames associated with substantial motion are not used in the combination, resulting in less blurring. Frame selection determines whether to integrate the information of a next frame for processing. The frames are selected based on similarity between frames, motion displacement parameters, or other characteristics.

U.S. Published Application No. 2008/0214934 (Ser. No. 11/713,209, the disclosure of which is incorporated herein by reference, describes embodiments of maximum intensity projection and selection of frames to be included in the maximum intensity projection image. The same selection or different selection criteria may be used for an integration, maximum intensity projection, or other combination. The non-selected ultrasound frames of data are not used for determining the display value or image.

The stationary contrast agents are displayed alone or combined with B-mode, integrated or MIP, or time-to-peak images. The different information is displayed at a same time as different images, such as in a dual screen format. Alternatively, the different information is combined or mixed. A linear or non-linear combination may be used. For example, a look-up table allows blending of two parameters in any function. The user may select which elements are blended and displayed and the relative weighting.

In one example embodiment, maximum intensity projection of the stationary contrast agent information is used for imaging during acquisition. The time-to-peak augments the contrast agent information. The time-to-peak associated with each spatial location is determined. Any function may be used. In one example time-to-peak, a further threshold is incorporated. $C_{MIP}(t)$ is the maximum intensity projection (maximum value from time 0 to time t) of contrast agent image C from time 0, immediately after destruction, to current time, t. $C_{BaselinePerusion}$ is the contrast agent image C at time 0, immediately after the destruction frames. $C_{BaselinePerfusion}=C_{MIP}(0)$. $C_{MaxPerfusion}$ is the contrast agent image C from time less than zero, immediately before the destruction frames. $C_{MaxPerfusion}$ represents the region fully perfused. The capture interval for the maximum intensity projection is selected by the user. If an indefinite interval is selected, the capture interval used in the time to peak calculation is replaced by a set value, such as 5 seconds.

On example time-to-peak algorithm applies a threshold and is:

$$\text{if } C_{MIP}(t) > timeToPeakThreshold \text{ then } T_{pk} = t \cdot \frac{255}{captureInterval}$$

If $C_{MIP}(t)$ is less than or equal to the threshold, then an event has not been reached during the interval t. The timeToPeakThreshld is 50, and the captureInterval is 5 in one example. The algorithm is for display in a range of 0-255.

Another example time-to-peak algorithm corrects for maximum and baseline perfusion and is:

$$\text{if } C_{MIP}(t) - C_{BaselinePerfusion} - timeToPeakScaleFactor \cdot C_{MaxPerfusion} >$$
$$timeToPeakThreshold \text{ then } T_{pk} = t \cdot \frac{255}{captureInterval}$$

If less than or equal to the threshold, then the event has not been reached in the interval t. With a timeToPeakScaleFactor=0.8, 80% of the maximum perfusion is used before the peak is declared. The timeToPeakThreshold may, in an example, be set to a small value, say 5 out of 255, to help reject noise.

In addition to time-to-peak information, an amount of motion is used to select which frames of data to include in the maximum intensity projection. A tracking box defines the region of interest for determining motion. For example, the tracking box is 33% of the range and 33% of the azimuth (lateral) in size relative to the field of view (100% is full height or width). The tracking box is centered in the field of view. Limits on the amount of motion may be included, such as only searching with 5% or less displacement in azimuth or range. The limits on motion define a search space.

Excessive in-plane or out of plane motion is identified. Frames of data associated with excessive or out-of-plane motion are not used in the maximum intensity projection to prevent inclusion of erroneous data and also prevent the search space from wondering. The motion is detected as part of, prior to, or after motion correction of acts 28 and 30. The motion is detected from the contrast agent information. In other embodiments, the motion is detected from tissue information.

The tracking box is repositioned by translation and/or rotation within the search space. For each position, a minimum sum of absolute differences is calculated. The position with the lowest value (minSAD) is determined.

An average sum of absolute differences (avgSAD) is also calculated. For each possible position, the sum of absolute differences is calculated. The resulting values across positions are averaged.

If the minSAD is near the avgSAD, the similarity may not be accurate. One or more functions to determine whether the similarity is subject to noise or errors may be used. For example, a minimum sum of absolute differences gray average is equal to the minSAD divided by the number of spatial locations in the tracking box. If the grey average is greater than a threshold (e.g., 20), then there may be excessive motion or other undesired information. As another example, a ratio of the minSAD to the avgSAD is calculated. If the ratio multiplied by 100 is greater than 30, then there may be excessive motion or other undesired information. Other functions may be used.

If undesired motion is found, the maximum intensity capture is shut off or the frame of data is not selected for projection. The center of the search space updates based on the previous motion tracking determination. If excessive motion is found, the center for searching may not be updated.

After selection, the frames of data are used for maximum intensity projection. The resulting image $C_{MIP}$ represents the maximum value of contrast agent response for each spatial location through the sequence. The maximum value or corresponding image value may be augmented with the time-to-peak information. For example, the brightness is increased for later arrivals—contrast agent with a later time-to-peak. One embodiment is represented by:

$$\tilde{C}_{MIP} = C_{MIP} + T_{pk} \frac{MaxMipAugmenationFromTpkdB}{bModeDynamicRange}$$

where bModeDynmicRange is the dynamic range of the B-mode information, and MaxMipAugmentationFromTpkdB is 10. As another example, the brightness of earlier arrivals is increased. On embodiment is represented by:

$$\tilde{C}_{MIP} = C_{MIP} + (255 - T_{pk}) \frac{MaxMipAugmenationFromTpkdB}{bModeDynamicRange}, \text{ if } T_{pk} > 0.$$

The time-to-peak information includes values for each spatial location. The time-to-peak information may be filtered, such as spatially smoothing with a two dimensional boxcar filter. For example, a 6×6 boxcar filter is used. Other filters with a predetermined or adjustable number of taps may be used.

Other acts may be performed. For example, the destruction act 32 is repeated after the combination and/or highlighting of acts 40 and/or 38. The acoustic energy for destruction may be focused at or to cover the stationary contrast agents. Sufficient energy to substantially destroy the identified contrast agents that are substantially stationary is transmitted. The resulting destruction may release drugs within or used to form the contrast agents. Where the contrast agents target specific tissue, the release occurs adjacent the specific tissue.

The destruction may be for therapeutic ultrasound. Ultrasound is used to generate heat at a region. The stationary contrast agents may indicate the appropriate region for therapeutic ultrasound. Other targeted treatment for molecular medicine may be used, such as causing cavitations with the contrast agent or in the tissue for therapy (e.g., to break a clot).

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for contrast agent enhanced medical diagnostic ultrasound imaging, the method comprising:
   generating a sequence of ultrasound frames of data representing, at least in part, information from contrast agents;
   tracking relative position between at least first and second ultrasound frames of data of the sequence;
   detecting substantially stationary contrast agents from the sequence as a function of the tracking and a consistency of response; and
   spatially aligning the first and second ultrasound frames of data as a function of the tracking;
   wherein detecting comprises identifying contrast agents in a substantially same location in a majority of spatially aligned ultrasound frames of data.

2. The method of claim 1 further comprising:
   for each spatial location in a region of interest, selecting a maximum value from the spatially aligned first and second ultrasound frames of data information; and
   generating a maximum intensity projection image as a function of the maximum values.

3. The method of claim 1 further comprising:
   highlighting the detected stationary contrast agents in a displayed image.

4. The method of claim 1 further comprising:
   destroying the substantially stationary contrast agents.

5. The method of claim 1 further comprising:
   selecting a subset of the ultrasound frames of data from the sequence, the selecting being a function of motion; and
   generating an integration or maximum intensity projection images from the ultrasound frames of data of the subset and not from ultrasound frames of data outside the subset.

6. The method of claim 1 wherein the ultrasound frames of data of the sequence correspond to tissue information and contrast agent information, wherein the tracking is performed with the tissue information and wherein the detecting is performed with the contrast agent information.

7. The method of claim 1 wherein detecting comprises detecting a cubic fundamental response from ultrasound signals.

8. The method of claim 1 wherein detecting comprises detecting contrast agent response and identifying spatial locations with consistent contrast agent response adjusted by the tracking.

9. In a tangible computer readable storage medium having stored therein data representing instructions executable by a programmed processor for contrast agent enhanced medical diagnostic ultrasound imaging, the storage medium comprising instructions for:
   detecting contrast agents;
   correcting for motion between frames of ultrasound data corresponding to the detected contrast agents; and
   identifying contrast agents that are substantially stationary from the motion corrected frames of ultrasound data by consistency of return from one or more spatial locations, wherein identifying comprises identifying spatial locations with contrast agents a threshold number of instances within a sequence of frames of ultrasound data.

10. The tangible computer readable medium of claim 9 wherein correction comprises tracking the motion and aligning the frames of ultrasound data as a function of the motion.

11. The tangible computer readable medium of claim 9 wherein detecting contrast agents comprises detecting a cubic fundamental response.

12. The tangible computer readable medium of claim 9 wherein correcting for motion comprises correcting for motion with B-mode data, and wherein identifying comprises identifying with contrast agent data of the detected contrast agents.

13. The tangible computer readable medium of claim 9 further comprising:
   combining data of the substantially stationary contrast agents from the frames of ultrasound data, the combining being an integration or a maximum intensity projection for each spatial location.

14. The tangible computer readable medium of claim 13 further comprising:
   not combining data from frames of data associated with a threshold amount of the motion.

15. The tangible computer readable medium of claim 9 further comprising:
   transmitting acoustic energy sufficient to substantially destroy the identified contrast agents that are substantially stationary.

16. The tangible computer readable medium of claim 9 further comprising:
   generating heat in a region indicated by the identified contrast agents that are substantially stationary.

17. A system for contrast agent enhanced medical diagnostic ultrasound imaging, the system comprising:
   a receive beamformer;
   an image processor operable to detect contrast agents from information output from the receive beamformer;
   a motion processor operable to stabilize for motion between frames of ultrasound data, and operable to determine contrast agents with substantially no movement between the stabilized frames of ultrasound data, the determining being a function of consistent response at one or more locations in a majority of the stabilized frames of ultrasound data; and
   a display operable to display an image of the contrast agents with substantially no movement uniquely colored.

18. The system of claim 17 further comprising:

a transmit beamformer operable to transmit a sequence of pulses;

wherein the receive beamformer is operable to output the information responsive to the sequence of pulses, the sequence of pulses increasing contribution of contrast agents relative to tissue in the information; and wherein the image processor comprises a B-mode detector, the stabilization being a function of B-mode data representing tissue.

19. The system of claim 17 wherein the motion processor is operable to combine the frames of ultrasound data, the image being a function of the combined frames of ultrasound data.

* * * * *